June 19, 1956 M. L. WHISLER Plant Pat. 1,486
ROSE PLANT
Filed Oct. 21, 1955
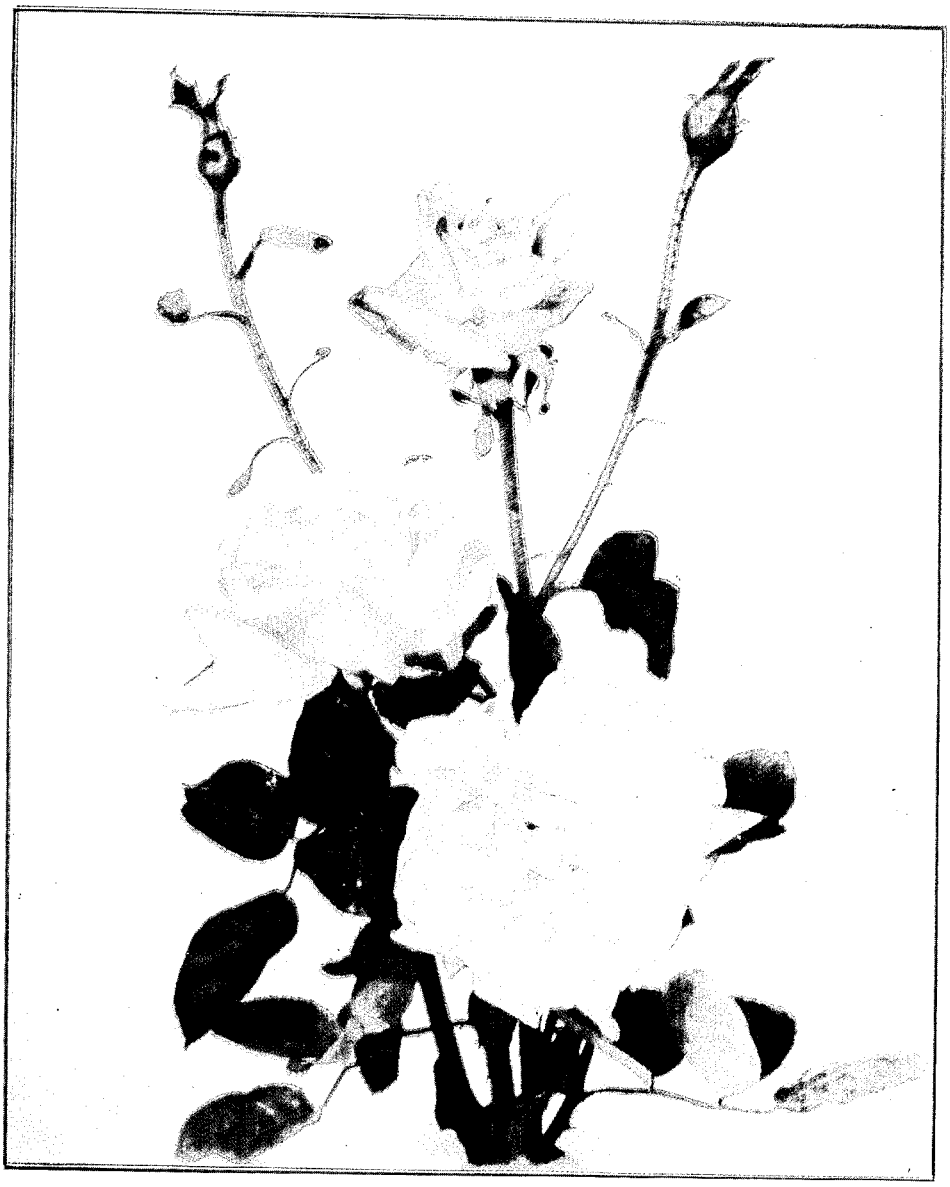
Inventor.
M. L. Whisler
By: Robb & Cobb
Attorneys.

United States Patent Office

Plant Pat. 1,486
Patented June 19, 1956

1,486

ROSE PLANT

Milton L. Whisler, Granada Hills, Calif., assignor to Germain's, Inc., Van Nuys, Calif., a corporation of California Application October 21, 1955, Serial No. 542,123

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Mission Bells" (Plant Patent No. 923).

As the result of this breeding, I have produced a new rose variety which is a substantial improvement over the parent variety "Mission Bells" which the new variety most nearly resembles. The principal outstanding features of the new variety which together characterize it as to novelty and distinctiveness are the vigorous and well-branched habits of growth of the plant, the deep glow of the flower petals and their improved substance and texture which give the blooms a long-lasting quality as cut flowers, and the habit of the blooms being borne singly on long cutting stems. These combined features definitely differentiate the new variety from its parents, as well as from all other varieties of its class of which I am aware.

Asexual reproduction of the new variety by budding, as performed by me at Saugus, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Half-hardy; bush; outdoor; seedling; for cut flowers and for garden decoration.
Class: Hybrid tea.
Breeding: Seedling.
*Seed parent.*—"Charlotte Armstrong."
*Pollen parent.*—"Mission Bells."
Propagation: Holds its distinguishing characteristics through succeeding propagations by budding.

FLOWER

Locality where grown and observed: Saugus, California.
Flowers borne: Singly to stem; on long, strong stems.
Quantity of bloom: Free, outdoors.
Continuity: Continuous.
Fragrance: Slight. Nature—Sweetbriar.
Bud:
*Peduncle.*—Medium length; medium caliper; erect; almost smooth; with numerous red prickles. Color—Scheeles Green, Plate 860/2, washed with Erythrite Red, Plate 0027 on surface in direct sunlight, and with hairs of Erythrite Red, Plate 0027.
*Before calyx breaks.*—Size—medium. Form—ovoid; with foliaceous appendages on the surface of the bud; with slender, much-cut foliaceous parts extending beyond the tip of the bud equal to ¼ of its length. Color—Scheeles Green, Plate 860/2, splotched with Erythrite Red, Plate 0027 on surfaces in direct sunlight.
*As calyx breaks.*—Color—Jasper Red, Plate 018.
*As first petal opens.*—Size—medium. Form—long; pointed. Color: outside—Jasper Red, Plate 018/1; inside—Geranium Lake, Plate 20/1.
*Opening.*—Opens up well.

Bloom:
*Size (when fully open).*—Medium; from 4 inches to 5 inches.
*Petalage.*—Double; from 25 to 30 petals; arranged regularly.
*Form.*—Cupped at first, but becoming open-cupped; petals being at first loosely cupped, but later becoming loosely rolled outward at maturity.
Petals:
*Texture.*—Thick; leathery; with inside velvety and outside satiny.
*Shape.*—Outside—round; intermediate—oval.

This description of a newly opened flower was made from a rose grown outdoors in the month of June, at Saugus, California:

*Color.*—Outer petal: outside surface—Azalea Pink, Plate 618; inside surface—Claret Rose, Plate 021/1. Intermediate petal: outside surface—Jasper Red, Plate 018/1; inside surface—Geranium Lake, Plate 20/1. Inner petal: outside surface—Scarlet, Plate 19/2; inside surface—Cherry Red, Plate 722.

This description was made from a rose that was open for three days outdoors in the month of June, at Saugus, California:

*Color.*—Outer petal: outside surface—Porcelain Rose, Plate 620/1; inside surface—Spinel Pink, Plate 0625. Inner petal: outside surface—French Rose, Plate 520; inside surface—Camellia Rose, Plate 622/1.
*General color effect.*—Newly opened flower—Vermillion, Plate 18/1. 3-days open—Geranium Lake, Plate 20/2.
*Behavior.*—Drop off cleanly; flowers not affected by weather.
*Flower longevity.*—On bush in garden—5 days in June. Cut roses grown outdoors and kept at living-room temperature—3 days in June.

REPRODUCTIVE ORGANS

Stamens: Many; arranged regularly about pistils. Color—Yellow Ochre, Plate 07/1.
Filaments: Medium length; most with anthers. Color—Apricot, Plate 609/1.
Anthers: Medium size; all open at once. Color—Yellow Ochre, Plate 07/1.
Pollen: Moderate. Color—Empire Yellow, Plate 603/1.
Pistils: Medium number.
Styles: Even; from short to medium length; thin; loosely bunched.
Stigma: Color—white.
Ovaries: All enclosed in calyx.
Hips: None.
Sepals: Permanent; long; some straight and some recurved. Color: outer surface—Scheeles Green, Plate 860/2, splotched with Erythrite Red, Plate 0027/2; inner surface—Fern Green, Plate 0862/1.
Seeds: None.

PLANT

Foliage:
*Leaves.*—Compound of 5 leaflets; normal abundance; medium size; moderately heavy and leathery.

*Leaflets.*—Shape—oval, with apex obtuse. Base—round. Margin—doubly serrate.

*Color.*—Mature: upper surface—Spinach Green, Plate 0960/1; under surface—Spinach Green, Plate 0960/3. Young: upper surface—Sage Green, Plate 000861, washed with Pansy Purple, Plate 928; under surface—Pansy Purple, Plate 928/3.

*Rachis (the supporting stem of the compound leaf).*—Medium caliper. Upper side—grooved; hairy. Under side—moderately hairy; prickly.

*Stipules.*—Medium length; narrow; with short points turning out at an angle of 45°.

*Disease resistance.*—Sometimes subject to mildew, but no evidence of blackspot has been observed, as compared with other varieties grown under comparable cultural conditions at Saugus, California.

Growth:

*Habit.*—Bushy; well-branched.

*Growth.*—Vigorous.

*Canes.*—Medium caliper.

*Main stems.*—Color—Scheeles Green, Plate 860/2. Thorns—few; medium length; straight; with short, broad base. Color—medium walnut brown. Prickles—none. Hairs—none.

*Branches.*—Color—Lettuce Green, Plate 861/2. Thorns—few; medium length; some straight and some hooked downward; with short, broad base. Color—medium walnut brown. Prickles—few. Color—light walnut brown. Hairs—none.

*New Shoots.*—Color—Erythrite Red, Plate 0027, washed with Scheeles Green, Plate 860/3. Thorns—few; medium length; some straight and some hooked downward; with short, broad base. Color—Ruby Red, Plate 827/1. Prickles—none. Hairs—none.

I claim:

A new and distinct variety of rose plant of the hybrid tea class, substantially as herein shown and described, characterized particularly as to novelty by the vigorous and well-branched habit of growth of the plant, the deep glow of its flower petals and their good substance and texture which give the bloom a long-lasting quality as a cut flower, and its habit of bearing the blooms singly on long cutting stems.

No references cited